United States Patent [19]

Nicolaides

[11] Patent Number: 5,503,818

[45] Date of Patent: Apr. 2, 1996

[54] ALUMINOSILICATE CATALYST, A PROCESS FOR THE MANUFACTURE THEREOF AND A PROCESS FOR THE SKELETAL ISOMERIZATION OF LINEAR OLEFINS

[75] Inventor: Christakis P. Nicolaides, Pretoria, South Africa

[73] Assignee: CSIR, Pretoria, South Africa

[21] Appl. No.: 332,064

[22] Filed: Nov. 1, 1994

[30] Foreign Application Priority Data

Nov. 1, 1993 [ZA] South Africa ............... 93/8130

[51] Int. Cl.$^6$ ............... C01B 33/26; B01J 21/00
[52] U.S. Cl. ............... 423/327.1; 502/76; 502/77; 502/344; 585/671
[58] Field of Search ............... 423/327.1; 585/671; 502/344, 77, 76

[56] References Cited

U.S. PATENT DOCUMENTS

| | | |
|---|---|---|
| 3,974,099 | 8/1976 | Lussier et al. . |
| 4,687,653 | 8/1987 | Arika et al. ............... 502/77 |
| 5,147,627 | 9/1992 | Chang et al. ............... 502/77 |
| 5,354,719 | 10/1994 | Gabelica et al. ............... 502/77 |

FOREIGN PATENT DOCUMENTS

| | | |
|---|---|---|
| 9976 | 4/1980 | European Pat. Off. . |
| 68708 | 1/1983 | European Pat. Off. . |
| 164939 | 12/1985 | European Pat. Off. . |
| 340868 | 11/1989 | European Pat. Off. . |
| 0501577A1 | 2/1992 | European Pat. Off. . |
| 0523838A2 | 6/1992 | European Pat. Off. . |
| 0574994A1 | 6/1993 | European Pat. Off. . |
| 913756 | 4/1945 | France . |
| 921318 | 2/1992 | South Africa . |

OTHER PUBLICATIONS

A Catalytic Method for the Quantitative Evaluation of Crystallinities of ZSM-5 Zeolite Preparations—Zeolites, 1992, vol. 12, pp. 685-689.
Catalytic Skeletal Isomerization of Linear Butenes to Isobutene—Catalysis Today, 18 (1993) 443-471.

*Primary Examiner*—E. Rollins Cross
*Assistant Examiner*—E. D. Irzinski
*Attorney, Agent, or Firm*—Lowe, Price, LeBlanc & Becker

[57] ABSTRACT

A novel family of substantially amorphous aluminosilicate catalysts and a process for the manufacture thereof are described. In the process, a source of silica, a source of alumina and a source of an alkali metal are mixed in an aqueous medium and then subjected to hydrothermal treatment at a temperature of from 20° C. to 200° C. for a period of from 1 hour to 250 hours, the reaction conditions and duration being selected so as to produce a solid which is substantially amorphous. The invention also extends to the use of the calalyst in acid catalyzed reactions such as the skeletal isomerization of normal olefins, in particular normal butene, and to the use of the catalyst as a support in metal catalyzed reactions.

23 Claims, 4 Drawing Sheets

ALUMINOSILICATE CATALYST, A PROCESS FOR THE MANUFACTURE THEREOF AND A PROCESS FOR THE SKELETAL ISOMERIZATION OF LINEAR OLEFINS

FIELD OF THE INVENTION

This invention relates to a novel family of aluminosilicate catalysts, to a process for the manufacture thereof, to the use of a catalyst in accordance with the invention in acid catalyzed reactions such as the skeletal isomerization of normal olefins, in particular normal butene, and to the use of a catalyst in accordance with the invention as a support in metal catalyzed reactions.

BACKGROUND TO THE INVENTION

Alkyl lead compounds, which have been conventionally used as anti-knock additives to motor fuels, exhibit undesirable properties such as the toxicity of the lead and their poisoning effect on catalytic converters. As a result, a need has arisen worldwide for other high octane compounds to be blended into the pool of fuel components available from refineries and synfuel plants.

Because of certain limits to the extent to which oil refineries and synfuel plants can increase the octane number of available fuel pool components, the demand for isoalkenes, especially in the $C_4$ to $C_5$ range, has risen considerably in recent years. One of the products which can be synthesized from isobutene is methyl tert-butyl ether (MTBE), which is a valuable octane boosting fuel additive. As a consequence, there is an increased demand for isobutene and for isomerization processes for the conversion of linear butenes to isobutene. Similarly, linear pentenes can be converted to isopentenes which could then be used to produce tert-amyl methyl ether (TAME).

Isomerization processes can be directed towards either skeletal isomerization or double bond isomerization. Skeletal isomerization is concerned with the reorientation of the molecular structure of a hydrocarbon, so as to increase the number of side chains. Double bond isomerization is concerned with the relocation of a double bond between carbon atoms forming part of a chain, and is not of great interest in the context of increasing octane values.

A large number of isomerization processes has been described in the literature, which has been summarized by Butler and Nicolaides in *Catalysis Today*, Vol. 18, 1993, 443 –471. Some of these processes rely on the use of metal oxides or crystalline aluminosilicates, some of them halogenated and others not, some of them containing metals and others not, some of them requiring a diluent in the isomerization reaction and others not. Most of the zeolite and halogenated alumina catalysts for the isomerization of linear butenes have a short life due to the formation of coke during the isomerization reaction, resulting from the occurrence of parasitic reactions such as cracking, polymerization and oligomerization, and a lack of stability frequently resulting in a rapid decrease of the conversion rate.

RSA Patent Application No 92/1318 and European Patent Application No 92200516.0 disclose a process for the conversion of a feedstock comprising linear olefins into a product enriched in branched olefins, which process comprises contacting the feedstock with a tectometallosilicate having a ferrierite crystal structure at a temperature between 150° C. and 450° C., and olefin partial pressure of more than 0.5 bar and a total pressure of between 0.5 and 25 bar. As will be appreciated by those skilled in the art, a tectometallosilicate which has a ferrierite crystal structure, is a fully or at least substantially crystalline material.

The use of the ferrierite zeolite, as a catalyst for the skeletal isomerization reaction of linear buteries, at an olefin partial pressure of Jess than or equal to 0.5 bar is described in European Patent Application 9320 1677.7. As expected, the lower partial pressures result in higher yields of the branched isomer.

European Patent Application No 92305090.0 discloses a process for structurally isomerizing a linear olefin of at least 4 carbon atoms to its corresponding methyl branched iso-olefin, which process comprises contacting a hydrocarbon feedstream containing at least one said linear olefin with an isomerizing catalyst at a temperature of from 340° C. to 650° C., said isomerizing catalyst comprising at least one zeolite with one or more one-dimensional pore structure having a pore size small enough to retard by-product and coke formation within the pore structure and large enough to permit entry of the linear olefin and allow formation and diffusion of the methyl branched iso-olefin. Likewise, it will be appreciated that a zeolite is considered by those skilled in the art, as a fully crystalline or at least substantially crystalline material. Examples of zeolites which can be used according to the aforementioned publication, include ferricrite, FU-9, NU-23, NU-10, ZSM-12, ZSM-22 etc, and molecular sieves such as SAPO-11, SAPO-31, SAPO-41, etc.

OBJECTS AND SUMMARY OF THE INVENTION

It is an object of the present invention to provide a catalyst which is more efficient than conventional aluminosilicate catalysts in acid catalyzed reactions such as the skeletal isomerization of olefins.

It is a further object of the invention to provide a catalyst which is capable of serving as a support for a metal and which is more efficient than conventional catalysts in metal catalyzed reactions.

Further objects and advantages of the invention will become apparent from a reading of the description of the invention and of the examples.

According to one aspect of the present invention, there is provided a process for the manufacture of a catalyst suitable for use in acid catalyzed reactions such as, for example, in the skeletal isomerization of olefins, or as a support in metal catalyzed reactions, including the steps of:

(a) mixing a source of alumina, a source of silica and a source of an alkali metal in an aqueous medium so as to form a reaction mixture;

(b) subjecting the reaction mixture of step (a) to hydrothermal treatment, at a temperature of from about 20° C. to about 200° C., for a period of from 1 hour to 250 hours, so as to allow the source of silica to react with the source of alumina to form an aluminosilicate solid and an aqueous solution, the reaction conditions and duration being selected such as to produce a solid which is substantially amorphous; and (c) separating the solid from the aqueous solution.

BRIEF DESCRIPTION OF THE DRAWINGS

Reference is now made to the drawings accompanying the application wherein.

Figure 1:
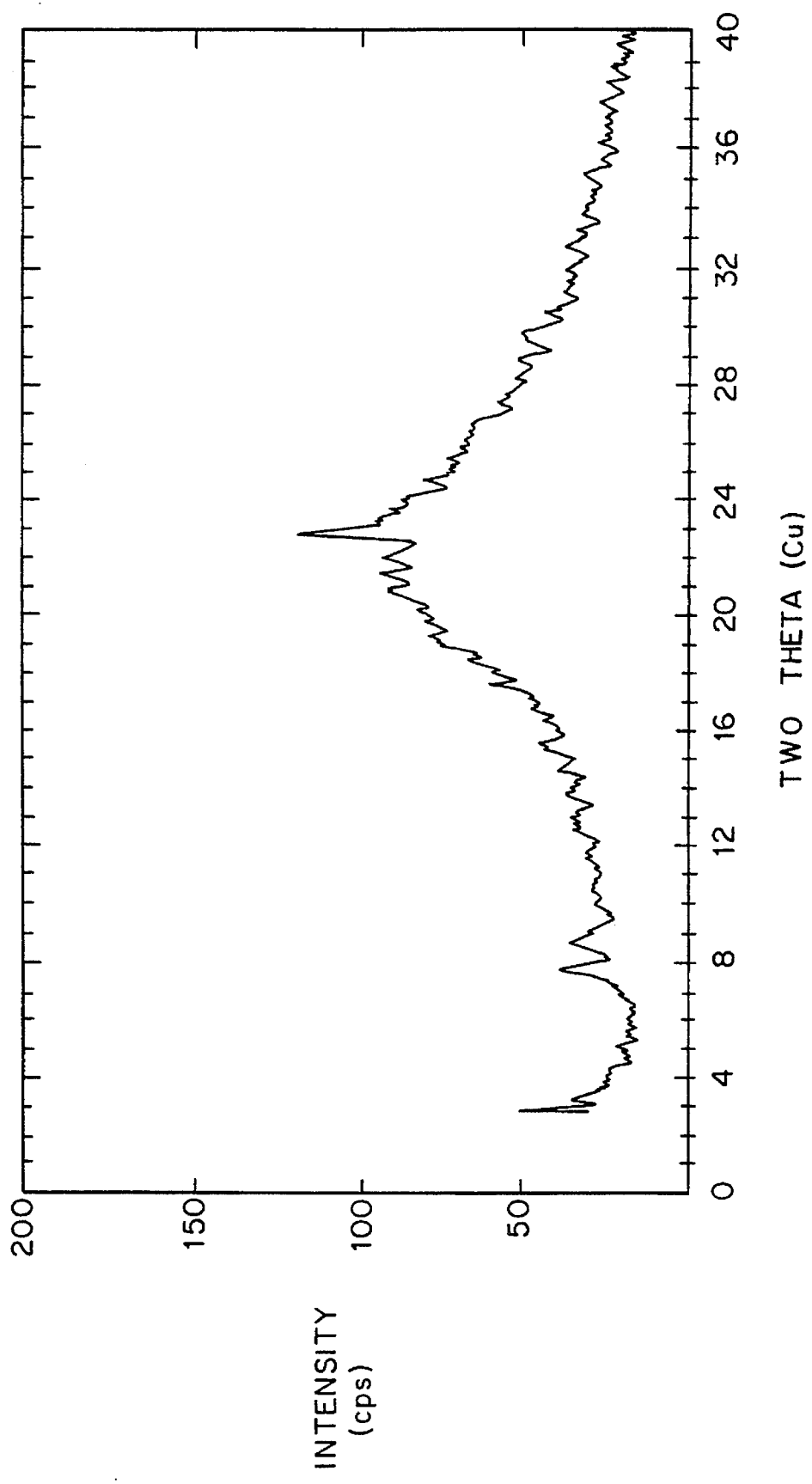
FIG. 1 is an X-ray diffractogram of NAS-27.

In this specification and in the claims, the expression "substantially amorphous" is intended to refer to a material which, when subjected to X-ray diffraction, appears to be at least about 30% amorphous.

It is furthermore to be understood that, in the context of a catalyst in accordance with the invention or a catalyst produced by the aforedisclosed process in accordance with the invention, the expressions "percent amorphous" and "percent crystalline" are intended to refer to the extent to which the crystallisation of a reaction mixture is complete and not to a mere mixture of physically discrete particles which are crystalline with physically discrete particles which are amorphous. It is also to be understood that % crystalline=100- % amorphous.

In the event that it is required to use the product of the aforedisclosed process in accordance with the invention as an acid catalyst or as a support for a metal catalyst, a source of phosphorus pentoxide may, in step (a) or in an additional step either preceding or following step (a), be mixed with the source of alumina, the source of silica and the source of an alkali metal. Alternatively or additionally, a source of metal oxide may be mixed with the source of alumina, the source of silica and the source of an alkali metal.

In order to influence the microporous characteristics of the catalyst, to the extent that it is crystalline, step (a) and/or step (b) may be carried out in the absence or presence of a template or seed material from a previous batch.

The reaction mixture of step (a) may be composed such as would be required for the production of a typical zeolite (for example, zeolite ZSM-5, ferrierite, Theta-1, etc), or such as would be required for the synthesis of a typical molecular sieve such as SAPO, MeAPO, MeAPSO, ELAPO and ELAPSO, etc.

Step (b) is preferably controlled, conducted or interrupted such that the solid obtained is at least 30%, more preferably at least about 50%, even more preferably, at least about 90%, amorphous. Although the solid may be partly amorphous and partly crystalline, such parts are produced from the same reaction mixture. The exact level of crystallinity required depends upon the particular reaction mixture and on the application of the resultant catalyst in an acid or metal catalyzed reaction.

The hydrothermal treatment of step (b) may be conducted with stirring or in the absence thereof.

Conveniently, the solid obtained frown step (c) is washed with water in a washing step (d), until the water is substantially free of template and excess ions.

Step (d) may be followed by a step (e) in which the solid obtained from step (d) is calcined in air at a temperature of from 300° C. to 800° C., preferably at a temperature of about 630° C., for a period of from 0.5 hour to 20 hours, preferably about 3 to 4 hours.

The process according to the invention may include an additional step (f) in which the calcined product of step (e) is subjected to ion exchange at a temperature of from about 10° C. to about 100° C., preferably from about 20° C. to about 30° C., with an aqueous solution of an ammonium salt, so as to yield an ammonium form of the catalyst. Optionally, the ion exchange step may be conducted using the strong acid itself, for example, hydrochloric acid.

The ammonium form of the catalyst may conveniently be subjected, in a further step (g), to further washing until it is substantially free of excess ions, whereafter it may be calcined in air, in a step (h), at a temperature of from 300° C. to 800° C., preferably about 550° C., for a period of from 0.5 hour to 20 hours, preferably about 3 hours, so as to yield a protonated form of the catalyst.

Suitable sources of silica include sodium silicate, colloidal silica, waterglass, fumed silica, silicic acid, silica gel and tetra ethyl orthosilicate.

Alumina may be sourced from sodium aluminate, simple aluminium salts or oxides or hydroxides of aluminum.

The alkali metal may be sourced from an alkali metal hydroxide or a simple salt of an alkali metal, or a combination thereof.

The template may be any one or more of the templates reported in the literature for the synthesis of ZSM-5, ferrierite, Theta-1 and of other crystalline aluminosilicates and molecular sieves, including tetra propyl ammonium bromide, pyridine, piperidine, ammonia, etc.

In step (a), the molar ratio of the template to the silica may vary from 1:200 to 1:1, preferably about 1:20 to 1:2, whilst tile molar ratio of silica to alumina in tile reaction mixture of step (a) may vary from 1000:1 to 1:1000, preferably about 500:1 to 5:1.

In a preferred embodiment of the process in accordance with the invention, in which the catalyst product of the process is to be used in the isomerization of linear buteries, sodium aluminate is mixed with an aqueous slurry of silica, whilst stirring, in a mutual ratio which would be required for the production of a ZSM-5 zeolite, to which mixture is then added a solution of tetrapropyl ammonium bromide, the resultant reaction mixture then being placed in an autoclave and stirred at a temperature typically in the range of 30° C. to 200° C., for a period of time ranging from about 1 hour to about 96 hours, the reaction being interrupted whilst the solids obtained from the reaction are still amorphous or at least substantially amorphous.

According to a second aspect of the invention, there is provided a catalyst suitable for use in acid catalysed reactions or as a support in metal catalysed reactions, comprising a mixed oxide reaction product of a source of silica and a source of alumina, wherein the molar ratio of silica to alumina present in the mixed oxide reaction product is from 1000:1 to 1:1000 and the mixed oxide reaction product is at least 30% amorphous.

The catalyst in accordance with the invention may be in the form of a molecular sieve and may comprise a mixed oxide reaction product of a source of silica, a source of alumina and a source of phosphorus pentoxide, wherein the molar ratio of silica to alumina present in the reaction product is towards the middle of the aforementioned range of 1000:1 to 1:1000, i.e. in the range of 1:1 to 1:10. In the event that the catalyst also comprises a metal oxide, the ratio of the metal oxide to alumina may be in the range of from 1:1 to 1:10.

In a preferred embodiment of the present invention, there is provided a catalyst suitable for the skeletal isomerization of linear olefins, particularly linear butene, comprising a substantially amorphous aluminosilicate, the molar ratio of $SiO_2:Al_2O_3$ present in the aluminosilicate being from 1000:1 to 10:1, preferably about 200:1, the catalyst being at least about 30% amorphous, preferably at least about 50% and more preferably at least about 90% amorphous. Even more preferably, the catalyst is at least about 95% amorphous.

In another preferred embodiment of the present invention, there is provided a catalyst suitable for the skeletal isomerization of linear olefins, particularly linear butene, comprising a substantially amorphous aluminosilicate, the molar ratio of $SiO_2:Al_2O_3$ present in the aluminosilicate being from 1000:1 to 10:1, preferably about 50:1 to 150:1, the catalyst being at least about 30% amorphous, preferably at least about 50% and more preferably at least about 90% amorphous.

Figure 2:
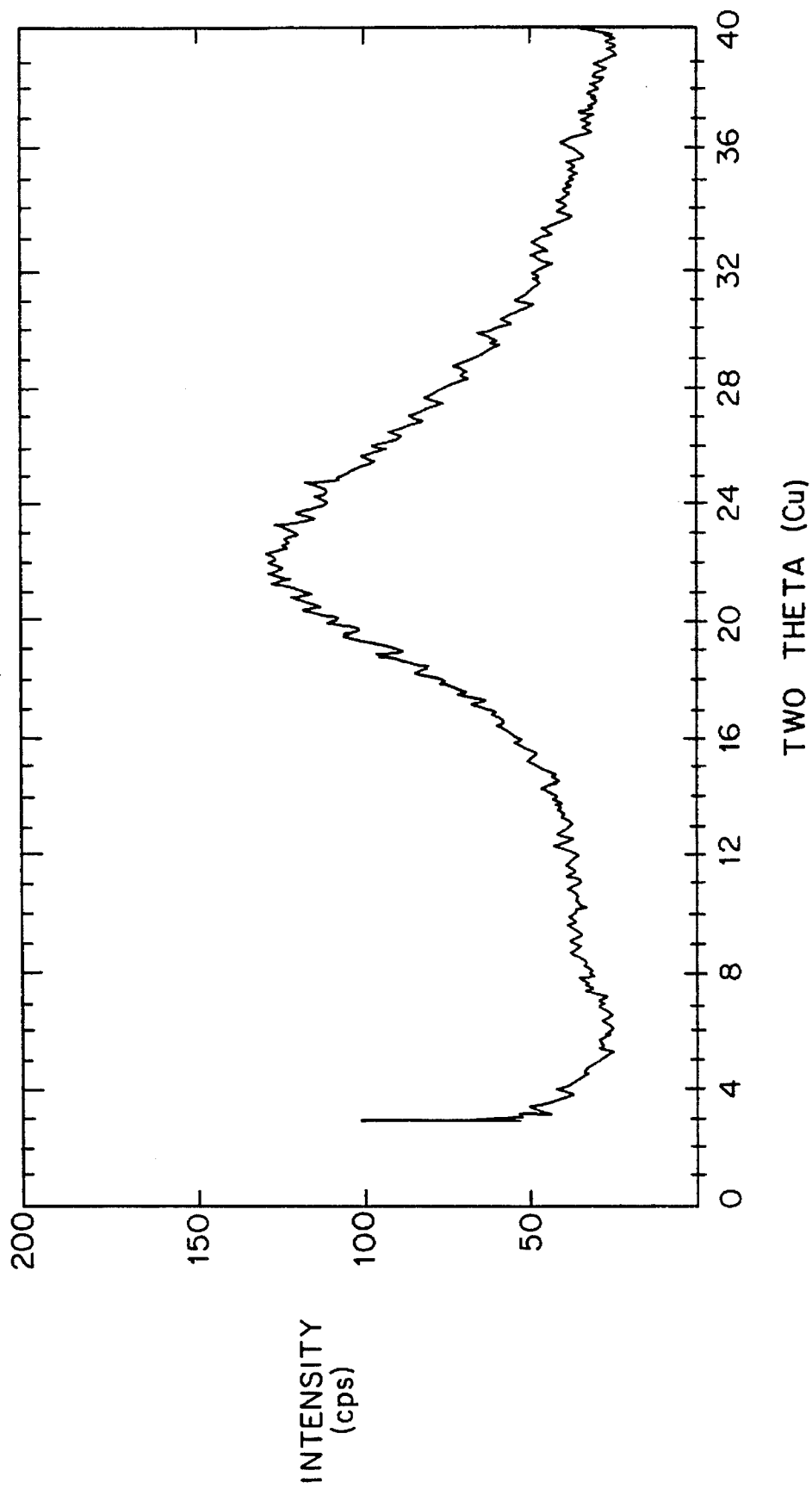
FIG. 2, is an X-ray diffractogram of NAS-24.

Typical products obtained from the process in accordance with the invention, have X-ray diffraction patterns exemplified by FIGS. 1 and 2.

According to a third aspect of the present invention, there is provided a process for the skeletal isomerization of linear olefins, including the step of contacting a feed stream containing the linear olefins with a catalyst as hereinbefore disclosed, at a temperature of from about 250° C. to about 550° C., at a total pressure of from 10 kPa absolute to about 5000 kPa absolute, preferably from 50 kPa to about 1000 kPa absolute, more preferably about 100 kPa absolute, at a mass hourly space velocity (MHSV) of from 0.2 to 20 per hour, preferably from about 0.5 to 10 per hour, more preferably about 1.0, to 10 per hour. The process may be conducted in the presence of a suitable diluent, the molar ratio of diluent to hydrocarbon feedstock being from 0.01:1 to 20:1, preferably from about 2:1 to about 15:1, more preferably from about 5:1 to about 12:1.

The diluent may be selected from nitrogen, water, an alkane, hydrogen or a mixture of any two or more thereof.

EXAMPLES

EXAMPLE 1

PREPARATION OF NAS-27

This catalyst is a member of the "first" series of NAS catalysts, which are based on a recipe for the preparation of ZSM-5 catalysts.

A sodium aluminate solution was prepared from 17.9 g of NaOH and 2.7 g of $Al(OH)_3$ to which 75 ml of distilled water was added. The mixture was heated and stirred until a clear solution was obtained (solution A).

Another solution (solution B) was prepared by mixing 29.7 g of tetrapropylammonium bromide with 75 ml of water and stirring it (without heating) until the solids dissolved.

A silica slurry (mixture C) was prepared from 80.4 g of fumed silica (Degussa, Aerosil 200) to which 650 ml of water was added, under vigorous stirring, until a smooth slurry was obtained.

To this slurry, solutions A and then B were added, again under vigorous stirring. An additional 440 ml of water was added to this final mixture which was then transferred to an autoclave where it was allowed to react at 90° C. for 72 hours, with stirring.

At the end of the hydrothermal treatment; the product was filtered and extensively washed with distilled water until the filtrates were free of bromide and hydroxide ions, as detected by the addition of silver nitrate. In order to remove the template, the purified solids were then placed in a furnace and calcined in air at 630° C. for 3.5 hours.

The calcined product was then converted to the ammonium form by ion exchange at room temperature with a 1M $NH_4Cl$ solution. The solids and solution (10 ml of solution/gram of solid) were placed in a beaker and stirred for one hour using an overhead stirrer. The ammonium solution was then decanted, fresh solution added and the ion exchange procedure repeated for a total of three times. The ammonium form of the catalyst was once again washed with distilled water until the filtrates were free of chloride ions.

The final step in the preparation of NAS-27 was the calcination of the ammonium form at 550° C. for 3 hours, in air, to give the $H^+$-form of the catalyst.

A sample of this catalyst was subjected to X-ray diffraction and the result thereof is shown in FIG. 1. The percentage XRD crystallinity of this sample of NAS-27 is 2% relative to a highly crystalline reference silicalite material. The method for determining crystallinaties is described in *Zeolites*, Vol 12, 1992, 685–689 by Itardenberg, Nicolaides et al.

EXAMPLE 2

Preparation of other catalysts in the "first" NAS series

Other variations of the "first" series of NAS catalysts were obtained using the above basic methodology by varying the amount of $Al(OH)_3$ added to solution A, or the amount of tetrapropylammonium bromide added to solution B or by varying the conditions of the hydrothermal treatment i.e. reaction temperature or time period employed. For example, using a synthesis temperature of 70° C. and a synthesis time of 72 hours, we obtained the amorphous sample NAS-4 whose X-ray diffractogram is shown in FIG. 2.

As would be appreciated by those skilled in the art, other series of NAS catalysts based on recipes for the synthesis of other zeolites or molecular sieves can be prepared by varying the nature of the template and/or the source of alumina and/or the source of silica and/or the reaction conditions.

EXAMPLE 3

Catalytic properties of "first" series of NAS catalysts

Figure 3:
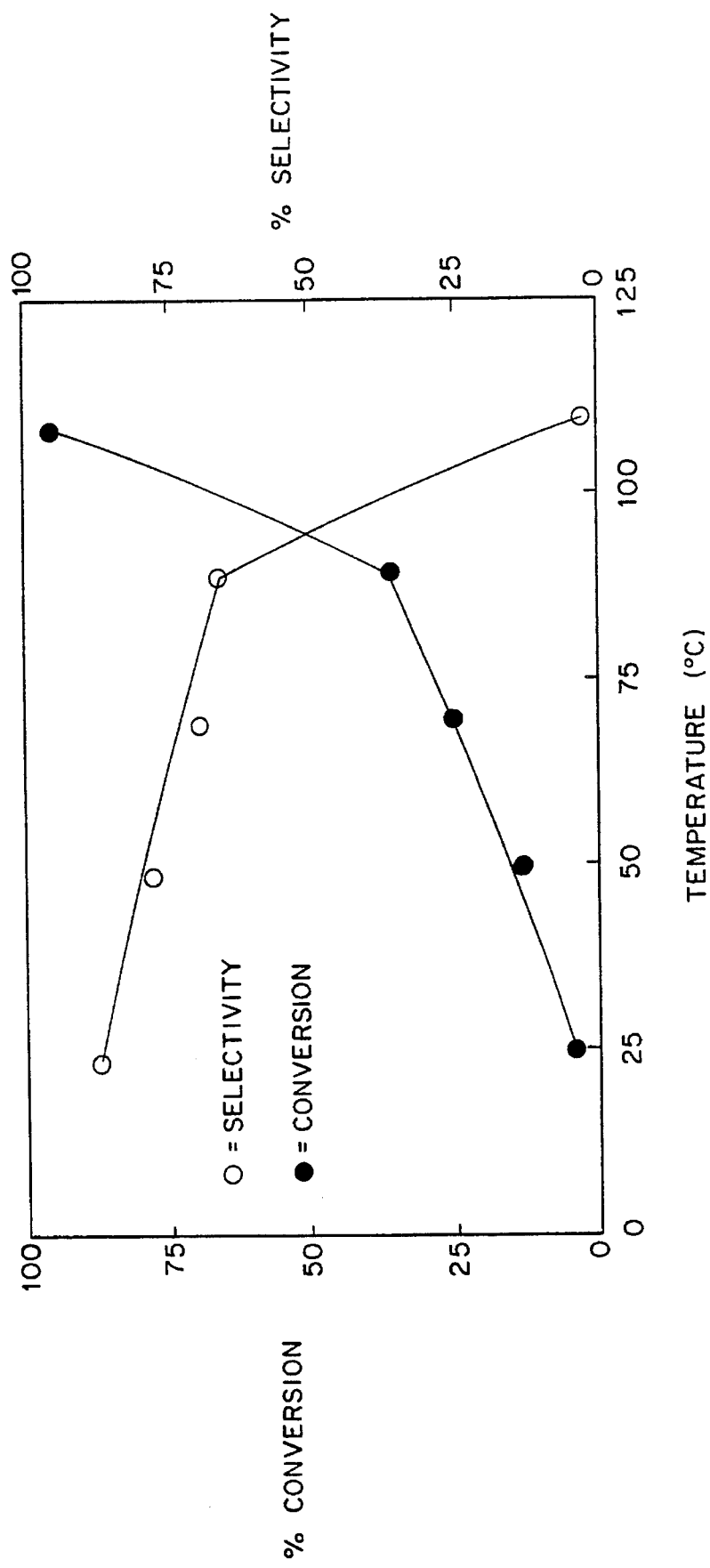
FIG. 3 is a graph showing the effect of synthesis temperature on activity and selectivity.

The catalytic properties of the first series of NAS catalysts for the skeletal isomerization of 1-butene were evaluated in a microreactor over a temperature range of 300° C. –500° C. and atmospheric pressure using 3 grams of the catalyst, MHSV=3, based on 1-butene, and a nitrogen flow rate of 0.57 liters per minute. The catalyst particle size was 45 to 160 micrometers. The first series of experiments was conducted to evaluate the influence of synthesis temperature (25° C. to 110° C.) on the catalytic activity and selectivity, with all other parameters being kept constant. The restfits in Table 1 and FIG. 3 show that the catalytic activity of catalyst samples prepared between 25° C. and 90° C. increased steadily. The catalyst identified as NAS-27, prepared at 90° C. as described above, was the most active and selective catalyst obtained since it produced the highest yield of isobutene. These studies showed therefore that with the amount of aluminium hydroxide and synthesis time used, a synthesis temperature of 90° C. provided the best catalyst in the first series of NAS catalysts, in terms of the butene isomerization reaction.

TABLE 1

Effect of synthesis temperature (at 500° C., MHSV = 3, nitrogen flow rate of 0.57 l/min)

| Catalyst batch | Synthesis temperature (°C.) | % Conv. | % Sel. | % Yield |
|---|---|---|---|---|
| NAS-21 | 25 | 3.9 | 87.9 | 3.4 |
| NAS-26 | 50 | 13.0 | 78.5 | 10.2 |
| NAS-4 | 70 | 24.8 | 69.6 | 17.3 |
| NAS-27 | 90 | 35.4 | 66.2 | 23.4 |
| NAS-28 | 110 | 95.7 | 2.6 | 2.5 |

EXAMPLE 4

Effect of catalytic reaction temperature

In another series of catalytic experiments, the effect of catalytic reaction temperature (350° C.–550° C.) on the activity and selectivity of the NAS-27 catalysts was investigated under the reaction conditions of MHSV=I and a butene:nitrogen dilution of 1:10.

Figure 4:
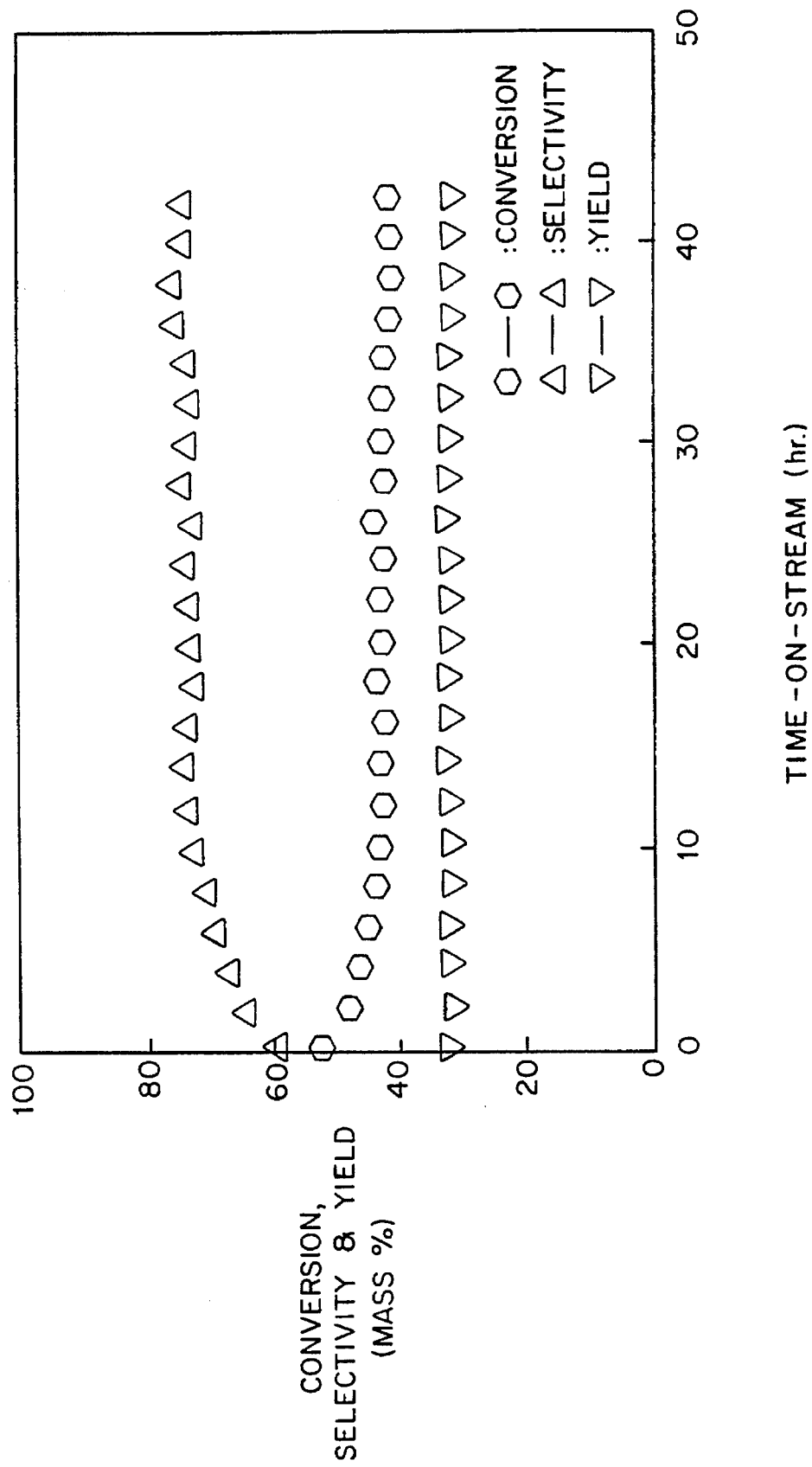
FIG. 4 is a graph showing the % conversion, selectivity and % yield versus time-on-stream for NAS-27.

The results are listed in Table 2 which show that the yield of isobutene increases with increasing reaction temperature between 350° C. and 500° C. Also, for all the reaction temperatures studied, no decrease in the % yield was observed with time-on-stream. FIG. 4 shows for example the results obtained at 500° C.

TABLE 2

Effect of reaction temperature on catalytic properties of NAS-27 (at MHSV = 1, dilution of 1:10 and at 20 hours on stream)

| Temperature (°C.) | % Conv. | % Sel. | % Yield |
|---|---|---|---|
| 350 | 69.8 | 17.1 | 11.9 |
| 400 | 43.7 | 41.0 | 17.9 |
| 450 | 39.8 | 63.2 | 25.2 |
| 500 | 48.7 | 65.2 | 31.8 |
| 550 | 36.1 | 83.3 | 30.1 |

EXAMPLE 5

Influence of type of diluent

In other work using catalyst NAS-27, the influence of water was studied under the same experimental conditions indicated above viz. MHSV=3, a nitrogen flow rate of 0.57 liters per minute, and reaction temperature of 500° C. These experiments showed that the presence of water did not contribute to a significant increase in isobutene yield although increasing the water/hydrocarbon ratio to 2.7 and decreasing the nitrogen flow rate to 0.02 liters per minute, did appear to increase the yield of the branched isomer slightly.

EXAMPLE 6

Influence of decreasing the amount of acid sites

The approach of decreasing the amount of acid sites by partial exchange of the catalysts with alkali metal cations such as sodium and potassium was also investigated using catalyst NAS-27. Batches of the cation-exchanged NAS-27 catalyst were produced by reacting the catalyst solids with a one molar KCl solution (10 ml of solutions/g of solid) for 20 hours at room temperature. After filtration, the solids were extensively washed with distilled water to remove any impregnated potassium chloride. Analysis of the exchanged NAS-27 catalyst showed a K/Al ratio of 0.22 which suggests that 22% of the acid sites have been neutralized. However, no improvement was observed in the catalytic performance.

From all the above results it is concluded that the NAS27 catalyst, which is prepared at 90° C. over a 72-hour period, provides the highest yield of isobutene under the conditions of MHSV=1, a temperature of 500° C. and a butene:nitrogen dilution of 1:10, as compared with the other catalyst batches and a commercial silica-alumina sample. This catalyst was also found not to deactivate under these reaction conditions and the % yield remained constant at 31% for over 40 hours on-stream.

EXAMPLE 7

Comparison with highly crystalline catalysts

The advantages of amorphous samples or samples of extremely low % crystallinity are further demonstrated by the results listed in Table 3 which were obtained using a highly crystalline ZSM-5 sample and its low-crystallinity analogues NAS27 and NAS-4, under the experimental conditions of 500° C., MHSV=1, a dilution of 1:10 and at 5 hours on-stream. The results clearly demonstrate the beneficial effect of lower levels of % crystallinity.

TABLE 3

The conversion of linear butenes to isobutene over ZSM-5-based catalysts.

| Catalyst | Synthesis temperature (°C.) | % crystallinity | % yield of isobutene |
|---|---|---|---|
| ZSM-5 | 150 | 86 | 4.9 |
| NAS-27 (this invention) | 90 | 2 | 31.4 |
| NAS-4 (this invention) | 70 | 0 | 22.0 |

EXAMPLE 8

Catalytic properties of second series of NAS catalysts

The second series of catalysts was prepared using the recipe for the synthesis of the zeolite ferrierite. The beneficial effect of the lower levels of % crystallinity are again demonstrated by the results listed in Table 4.

TABLE 4

The conversion of linear butenes to isobutene over ferrierite-based catalysts (at 350° C. and MHSV = 2 and at 48 hours on-stream)

| Catalyst | % Crystallinity | % Yield of isobutene |
|---|---|---|
| NAS-112 | 24 | 44.0 |
| NAS-113 | 56 | 38.9 |
| NAS-114 | 63 | 33.0 |
| NAS-115 | 67 | 31.7 |
| Shell Patent* | "essentially ferrierite" | 40.1 |

*Shell European Patent Application No 92200516.0.

EXAMPLE 9

Comparison with physical mixtures of crystalline and amorphous material

To demonstrate that the results shown in Table 4 are due to the percentage crystallinity of the as-synthesized sample, i.e. the ferrierite based NAS catalyst, and not due to the dilution of the catalyst with an amorphous phase, catalytic properties of physical mixtures prepared from the crystalline NAS-114 and in inactive batch NAS-116 were examined, where "inactive" implies no reaction of the butenes in any direction (no skeletal isomerization, no cracking and no oligomerization). The results obtained at 350° C., MHSV=2 and at 20 hours on-stream are listed in Table 5.

TABLE 5

% Crystallinity vs % dilution (at 350° C. and MHSV = 2 and at 20 hours on-stream)

| Catalyst | % Crystallinity | % Yield of isobutene |
|---|---|---|
| NAS-112 | 24 | 42.7 |
| NAS-114 | 63 | 22.8 |
| NAS-116 | 0 | 0 |
| 66% NAS-114 + 34% NAS-116 | "42" | 21.1 |
| 38% NAS-114 + 62% NAS-116 | "24" | 14.6 |
| 28% NAS-114 + 72% NAS-116 | "18" | 14.4 |

I claim:

1. A process for the manufacture of a catalyst suitable for use in acid catalyzed reactions, or as a support in metal catalysed reactions, including the steps of:
   (a) mixing a source of alumina, a source of silica and a source of an alkali metal in an aqueous medium so as to form a reaction mixture;
   (b) subjecting the reaction mixture of step (a) to hydrothermal treatment, at a temperature of from 20° C. to 200° C., for a period of from 1 hour to 250 hours, so as to allow the source of silica to react with the source of alumina to form an aluminosilicate solid and an aqueous solution, the reaction conditions and duration being selected such as to produce a solid which is at least 76% amorphous; and
   (c) separating the solid from the aqueous solution.

2. A process as claimed in claim 1, wherein, in step (a), at least one of a source of phosphorus and a source of metal is mixed with the source of alumina, the source of silica and the source of an alkali metal.

3. A process as claimed in claim 1, wherein step (a) is carried out in the presence of a suitable template.

4. A process as claimed in claim 1, wherein step (b) conditions and durations are selected such that the solid obtained is at least 90% amorphous.

5. A process as claimed in claim 1, wherein tile solid obtained from step (c) is washed with water in a washing step (d), until the water is substantially free of excess ions.

6. A process as claimed claim 5, wherein step (d) is followed by a step (e) in which the solid obtained from step (d) is calcined in air at a temperature of from 300° C. to 800° C., for a period of from 0.5 hours to 20 hours.

7. A process as claimed in claim 6, including an additional step (f) in which the calcined product of step (e) is subjected to ion exchange at a temperature of from 10° C. to 100° C., with an aqueous solution of an ammonium salt or of a strong acid.

8. A process as claimed in claim 7, wherein the ammonium form of the catalyst is subjected, in a further step (g), to further washing until it is substantially free of excess ions.

9. A process as claimed in claim 8, wherein, subsequent to step (g), the ammonium form of the catalyst is calcined in air, in a step (h), at a temperature of from 300° C. to 800° C.

10. A process as claimed in claim 1, wherein the source of silica is selected from sodium silicate, colloidal silica, waterglass, fumed silica, silicic acid, silica gel, tetra ethyl orthosilicate, or a combination thereof.

11. A process as claimed in claim 1, wherein the source of alumina is selected from sodium aluminate, a simple aluminium salt, an oxide of aluminium, a hydroxide of aluminium, or a combination thereof.

12. A process as claimed in claim 3, wherein the template is selected from tetra propyl ammonium bromide, pyridine, piperidine, ammonia, or a combination thereof.

13. A process as claimed in claim 12, wherein, in step (a), the molar ratio of the template to the silica is between 1:200 and 1:1.

14. A process as claimed in claim 1, wherein, in step (a), the molar ratio of silica to alumina in the reaction mixture is between 1000:1 and 1:1000.

15. A catalyst suitable for use in acid catalysed reactions or as a support in metal catalysed reactions, comprising a mixed oxide reaction product of a source of silica and a source or alumina, wherein the molar ratio of silica to alumina present in the mixed oxide reaction product is from 1000:1 to 1:1000 and the mixed oxide reaction product is at least 76% amorphous.

16. A catalyst as claimed in claim 15, comprising a mixed oxide reaction product of a source of silica, a source of alumina and a source of phosphorus pentoxide, wherein the molar ratio of silica to alumina present in the reaction product is in the range of 1:1 to 1:10.

17. A catalyst as claimed in claim 16, comprising a metal oxide, the ratio of the metal oxide to alumina being from 1:1 to 1:10.

18. A process for the manufacture of a catalyst suitable for use in acid catalyzed reactions, or as a support in metal catalyzed reactions, comprising the steps of:
   a) forming an aqueous solution of sodium aluminate, an aqueous solution of a template, and a slurry of silica, the sodium aluminate solution and template solution then being mixed with the silica slurry in such manner as to produce a reaction mixture wherein the molar ratio of silica to alumina varies from about 1000:1 to 1:1000 and the molar ratio of template to silica varies from about 1:200 to 1:1;
   b) subjecting the reaction mixture of step (a) to hydrothermal treatment by heating the mixture at a temperature of from about 30° C. to 200° C. for a period of time ranging from about 1 hour to about 96 hours, the reaction conditions and duration of reaction being selected so as to produce a solid which is at least 76% amorphous; and
   c) separating the solid from the aqueous solution.

19. A process according to claim 18, wherein the molar ratio of silica to alumina in the reaction mixture varies from about 500:1 to 5:1, and the molar ratio of template to silica varies from about 1:20 to 1:2.

20. A process according to claim 18 wherein the template is tetrapropyl ammonium bromide and the silica is fumed silica.

21. The process according to claim 18 wherein the reaction conditions and duration are selected so as to produce a solid which is at least 90% amorphous.

22. The process according to claim 1 wherein the catalyst or support produced is a zeolite or a molecular sieve.

23. The process according to claim 22, wherein the zeolite or molecular sieve is a ZSM 5 or a ferrierite.

* * * * *